United States Patent
Ouchi

(10) Patent No.: US 6,206,904 B1
(45) Date of Patent: Mar. 27, 2001

(54) FOREIGN BODY-RECOVERING INSTRUMENT FOR ENDOSCOPE

(75) Inventor: Teruo Ouchi, Saitama (JP)

(73) Assignee: Ashai Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/327,464

(22) Filed: Jun. 8, 1999

(30) Foreign Application Priority Data

Jun. 12, 1998 (JP) ............................................... P10-164651

(51) Int. Cl.⁷ ........................... A16B 17/28; A16B 01/012
(52) U.S. Cl. ........................... 606/207; 606/205; 600/104
(58) Field of Search ........................... 606/106, 113, 606/127, 205, 206, 207, 174; 600/104, 152, 154

(56) References Cited

U.S. PATENT DOCUMENTS

| | | | |
|---|---|---|---|
| 893,055 | * 7/1908 | Conner | 81/3.41 |
| 2,060,366 | * 11/1936 | Dunlap | 119/806 |
| 2,114,695 | * 4/1938 | Anderson | 606/206 |
| 2,137,710 | * 11/1938 | Anderson | 606/206 |
| 3,989,049 | * 11/1976 | Yoon | 128/831 |
| 4,085,743 | * 4/1978 | Yoon | 606/140 |
| 4,374,523 | * 2/1983 | Yoon | 606/141 |
| 4,393,872 | * 7/1983 | Rezuik et al. | 604/264 |
| 4,467,802 | * 8/1984 | Maslanka | 606/206 |
| 5,228,451 | * 7/1993 | Bales et al. | 600/564 |
| 5,609,599 | * 3/1997 | Levin | 606/153 |
| 5,667,525 | * 9/1997 | Ishibashi | 604/206 |
| 5,746,747 | * 5/1998 | McKeating | 606/114 |
| 5,849,022 | * 12/1998 | Sakashita et al. | 606/174 |
| 5,944,728 | * 8/1999 | Bates | 606/127 |
| 6,086,606 | * 8/2000 | Kknodel et al. | 606/208 |
| 6,102,910 | * 8/2000 | Boebel et al. | 606/52 |

\* cited by examiner

Primary Examiner—Paul J. Hirsch
Assistant Examiner—Michael B. Priddy
(74) Attorney, Agent, or Firm—Greenblum & Bernstein, P.L.C.

(57) ABSTRACT

A foreign body-recovering instrument for an endoscope in which a plurality of foreign body-catching arms are provided at the distal end of a flexible sheath so that the foreign body-catching arms are opened or closed by remote control from the proximal end of the sheath. The foreign body-recovering instrument has engaging portions serving as hooks for catching a foreign body. The engaging portions are formed on the respective outer sides of the foreign body-catching arms.

16 Claims, 16 Drawing Sheets

FOREIGN BODY-RECOVERING INSTRUMENT FOR ENDOSCOPE

BACKGROUND OF THE INVENTION

The present disclosure relates to subject matter contained in Japanese Patent Application No. 10-164651 (filed on Jun. 12, 1998), which is expressly incorporated herein by reference in its entirety.

1. Field of the Invention

The present invention relates to a foreign body-recovering instrument for an endoscope that is removably inserted into an instrument-inserting channel of an endoscope to recover a foreign body from a body cavity, for example, a swallowed dental crown.

2. Description of the Prior Art

In general, a foreign body-recovering instrument for an endoscope has a plurality of foreign body-catching arms provided at the distal end of a flexible sheath that is removably inserted into an instrument-inserting channel of an endoscope. The foreign body-catching arms are opened or closed by remote control conducted at the proximal end of the sheath. Each foreign body-catching arm has a claw-like portion projecting from the inner side thereof. The claw-like portion is pressed against a foreign body when the foreign body-catching arms are closed to hold the foreign body.

In actual use of such a conventional foreign body-recovering instrument, a foreign body is caught by pinching it with the foreign body-catching arms from outside the foreign body.

As shown in FIGS. 22 to 24 by way of example, the foreign body to be recovered may be an object having a smooth surface such as a dental crown 101, or a thin metal piece such as a coin 102, or a tubular small article 103. In such a case, the foreign body is slippery and hence difficult to pinch with the foreign body-catching arms 50. Therefore, there are not a few cases where it is difficult to recover the foreign body.

In particular, when a foreign body 100 is lodged in a narrow tubular cavity such as a bronchial tube as shown in FIG. 25, it is difficult to open the foreign body-catching arms 50 in excess of the outer diameter of the foreign body 100 and hence impossible to pinch it. Accordingly, it is extremely difficult to recover the foreign body 100.

SUMMARY OF THE INVENTION

An object of the present invention is to provide a foreign body-recovering instrument for an endoscope whereby a foreign body that is difficult to catch and recover by pinching can be readily caught and recovered, depending upon the shape of the foreign body.

Other objects and advantages of the present invention will become apparent from the following detailed description of illustrated embodiments of the invention.

According to the present invention, there is provided a foreign body-recovering instrument for an endoscope in which a plurality of foreign body-catching arms are provided at the distal end of a flexible sheath so that the foreign body-catching arms are opened or closed by remote control from the proximal end of the heath. The foreign body-recovering instrument has engaging portions serving as hooks for catching a foreign body. The engaging portions are formed on the respective outer sides of the foreign body-catching arms.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
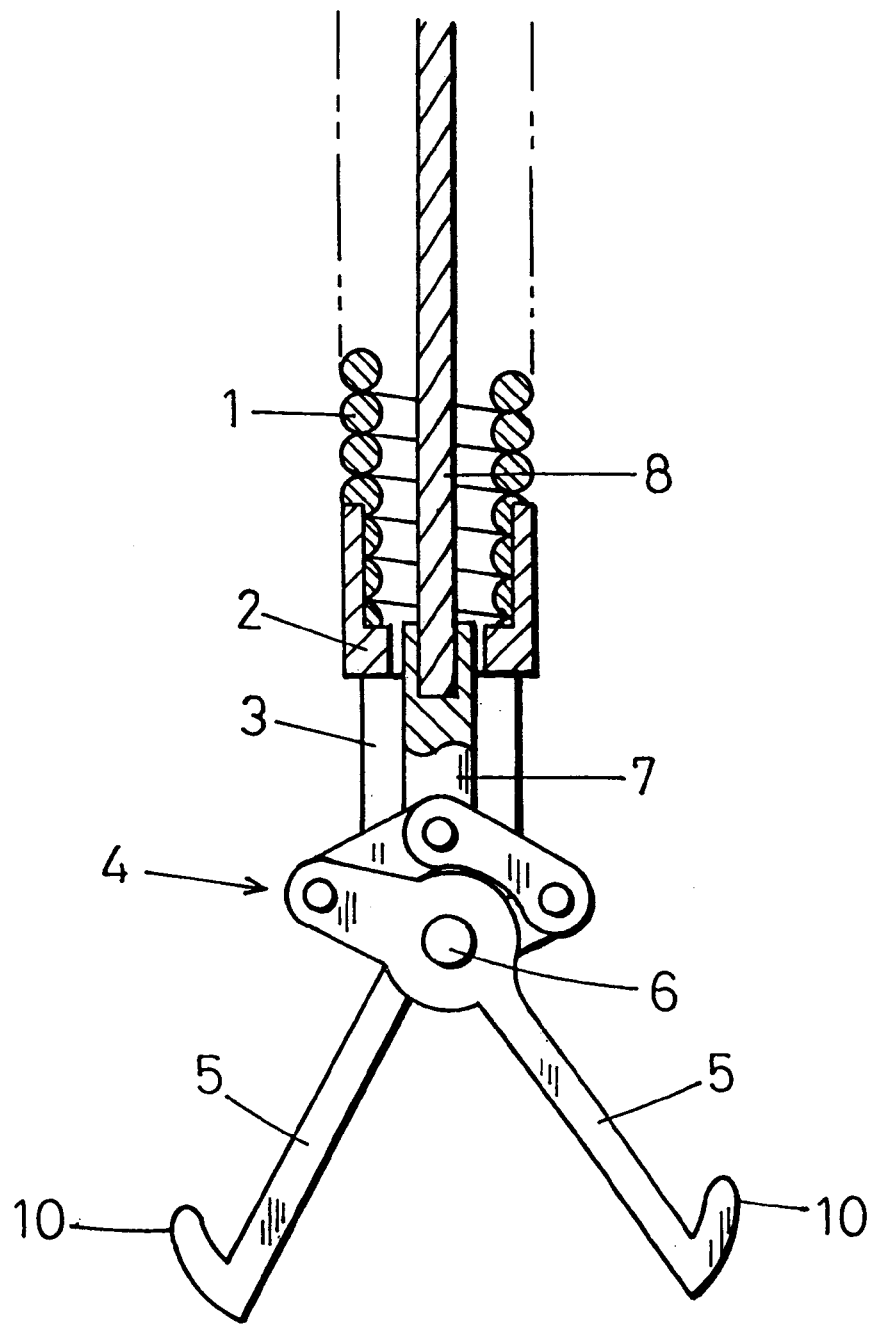
FIG. 1 is a sectional side view of a distal end portion of a foreign body-recovering instrument for an endoscope according to a first embodiment of the present invention, showing a state where foreign body-catching arms are open.
Figure 2:
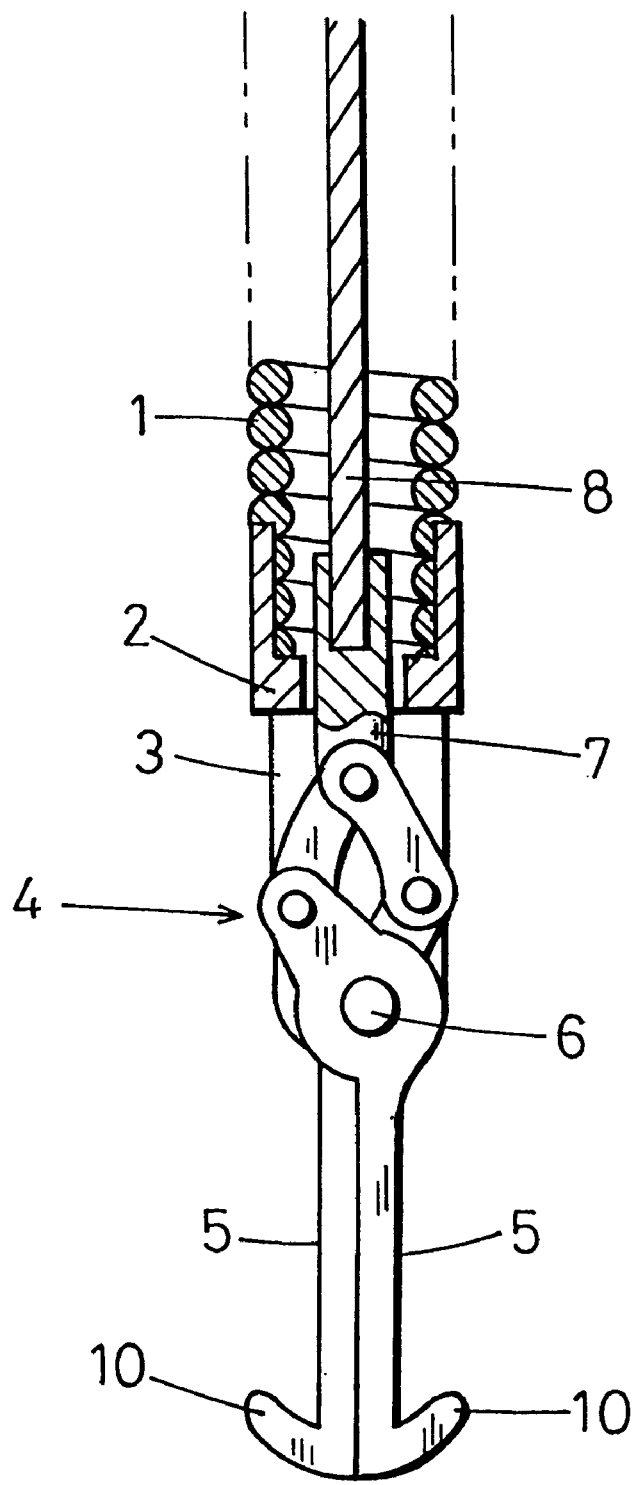
FIG. 2 is a sectional side view of the distal end portion of the foreign body-recovering instrument according to the first embodiment of the present invention, showing a state where the foreign body-catching arms are closed.

FIGS. 1 and 2 show a distal end portion of a foreign body-recovering instrument for an endoscope according to a first embodiment of the present invention. A flexible sheath 1 is removably inserted into an instrument-inserting channel of an endoscope (not shown). A coil pipe is used as the sheath 1. The coil pipe is formed by close-winding a stainless steel wire with a uniform diameter. The sheath 1 has a diameter of the order of from 1.5 millimeters to 2 millimeters and a length of the order of from 1.5 meters to 2 meters.

A support frame 2 is rigidly secured to the distal end of the sheath 1. The support frame 2 is provided with a slit 3. A pantograph-shaped link mechanism 4 is placed in the slit 3. A pair of foreign body-catching arms 5 are connected to the link mechanism 4. The foreign body-catching arms 5 are rotatably supported by a pivot shaft 6 in the vicinity of the distal end of the support frame 2. The foreign body-catching arms 5 project forward.

A wire-connecting shaft 7 is connected to the rear end of the link mechanism 4. The distal end of a control wire 8 is connected and secured to the wire-connecting shaft 7. The control wire 8 is axially movably inserted in the sheath 1. The movement of the control wire 8 is controlled at a control part (not shown) that is connected to the proximal end of the sheath 1.

By virtue of the above-described arrangement, the link mechanism 4 is operated by axially moving the control wire 8 from the proximal end of the sheath 1, thereby enabling the foreign body-catching arms 5 to be opened or closed in a beaklike manner about the pivot shaft 6. It should be noted that FIG. 1 shows a state where the foreign body-catching arms 5 are opened by pushing the control wire 8 toward the distal end of the sheath 1. FIG. 2 shows a state where the foreign body-catching arms 5 are closed by pulling the control wire 8 toward the proximal end of the sheath 1.

The pair of foreign body-catching arms 5 are each formed in an elongate rod-like shape. Each foreign body-catching arm 5 has an engaging portion 10 at the distal end thereof. The engaging portion 10 projects outward from the outer side of each foreign body-catching arm 5 as viewed in the direction in which the foreign body-catching arm 5 is opened or closed. The engaging portion 10 is formed in the shape of an L that is bent at an acute angle to serve as a hook for catching a foreign body that is to be recovered from a body cavity. The way in which the foreign body-catching arms 5 are used will be described later.

Figure 3:
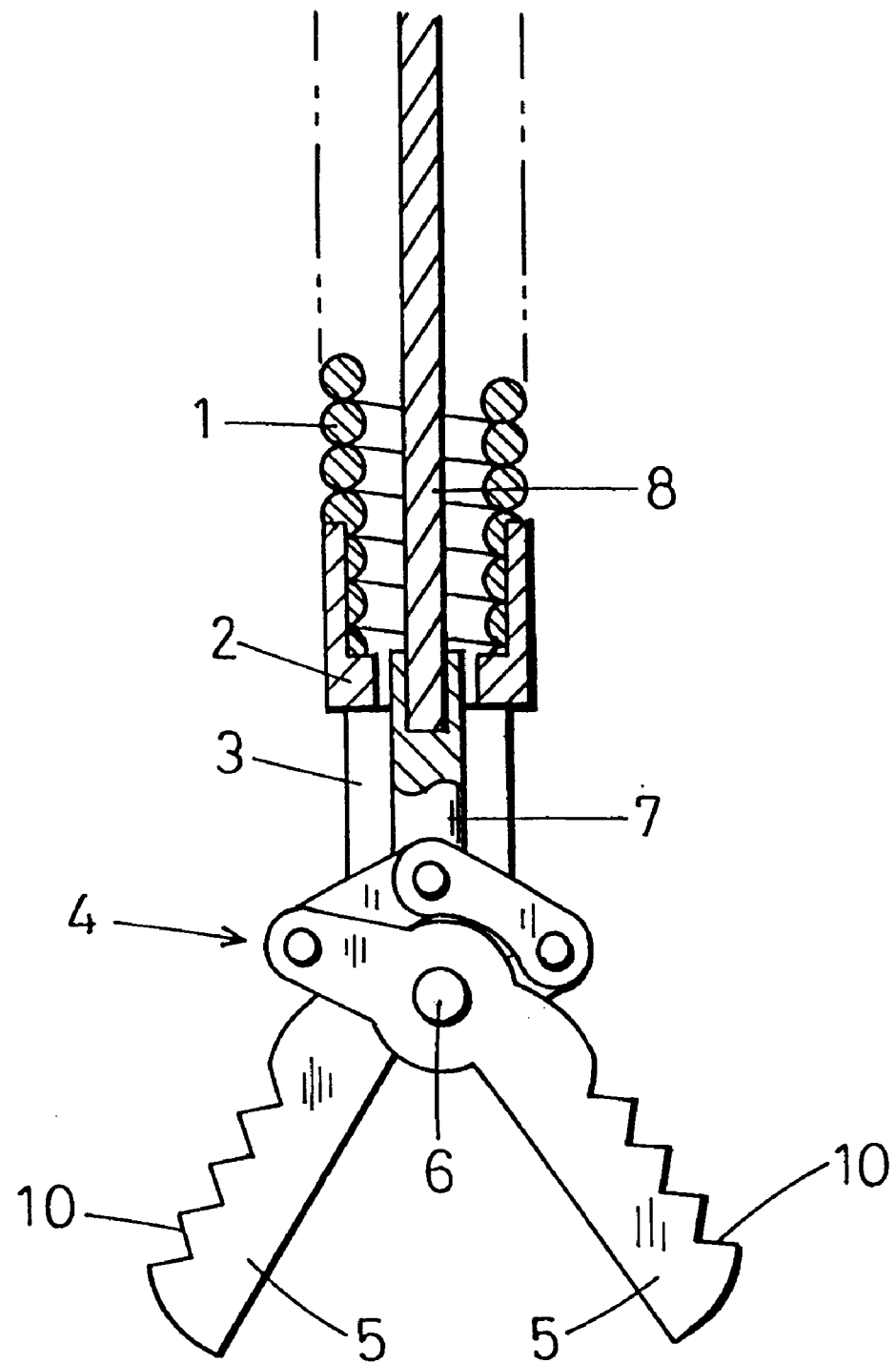
FIG. 3 is a sectional side view of a distal end portion of a foreign body-recovering instrument for an endoscope according to a second embodiment of the present invention, showing a state where foreign body-catching arms are open.
Figure 4:
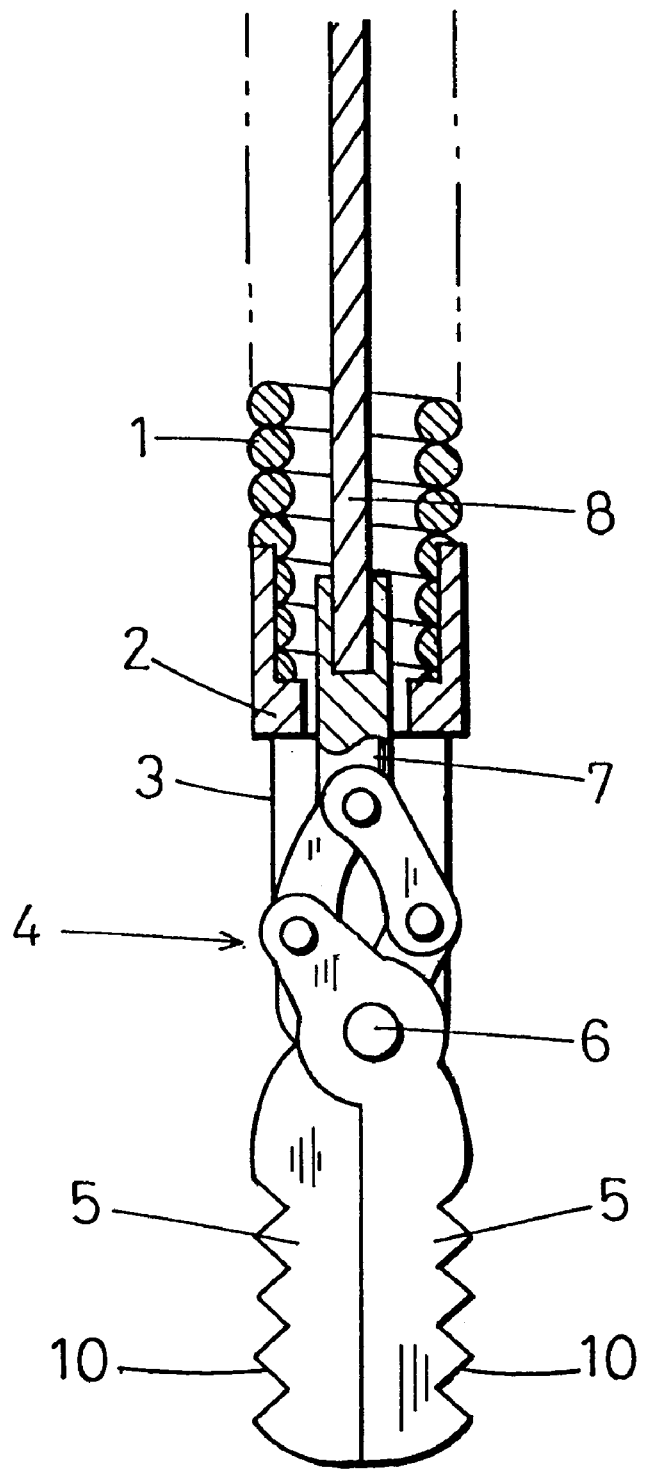
FIG. 4 is a sectional side view of the distal end portion of the foreign body-recovering instrument according to the second embodiment of the present invention, showing a state where the foreign body-catching arms are closed.

FIGS. 3 and 4 show a distal end portion of a foreign body-recovering instrument for an endoscope according to a second embodiment of the present invention. FIG. 3 shows a state where the distal end portion of the foreign body-recovering instrument is open. FIG. 4 shows a state where the distal end portion of the foreign body-recovering instrument is closed. A pair of foreign body-catching arms 5 each have an engaging portion 10 that acts as a hook for catching a foreign body that is to be recovered from a body cavity. The engaging portion 10 comprises serrate unevenness (notches) formed on the outer surface of each foreign body-catching arm 5 as viewed in the open-close direction of the foreign body-catching arm 5. The arrangement of the rest of this embodiment is the same as in the first embodiment.

Figure 5:
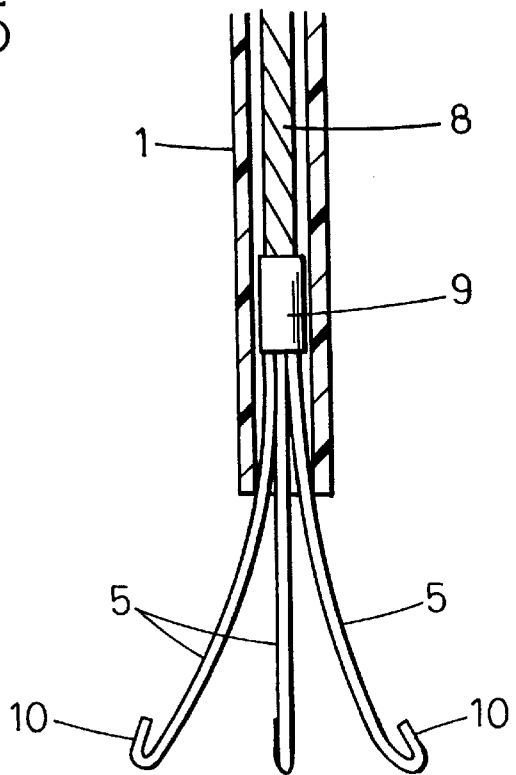
FIG. 5 is a sectional side view of a distal end portion of a foreign body-recovering instrument for an endoscope according to a third embodiment of the present invention, showing a state where foreign body-catching arms are open.
Figure 6:
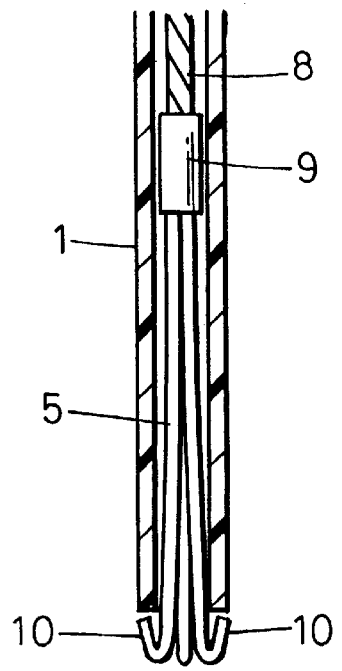
FIG. 6 is a sectional side view of the distal end portion of the foreign body-recovering instrument according to the third embodiment of the present invention, showing a state where the foreign body-catching arms are closed.

FIGS. 5 and 6 show a distal end portion of a foreign body-recovering instrument for an endoscope according to a third embodiment of the present invention. FIG. 5 shows a state where the distal end portion of the foreign body-recovering instrument is open. FIG. 6 shows a state where the distal end portion of the foreign body-recovering instrument is closed. In this embodiment, a flexible tube, e.g. a tetrafluoroethylene resin tube, is used as the sheath 1.

Four foreign body-catching arms 5 are provided at intervals of about 90 degrees as viewed from the front side (from the bottom of the figures). Each foreign body-catching arm 5 is formed from a resilient stainless steel wire or the like that is smoothly curved so as to expand outward.

It should be noted that the number of foreign body-catching arms 5 is not necessarily limited to four. For example, three foreign body-catching arms 5 may be disposed at intervals of about 120 degrees. Alternatively, two foreign body-catching arms 5 may be spaced at an angle of about 180 degrees. It is also possible to adopt other arrangements of foreign body-catching arms 5. The same is true in the following embodiments.

A plurality of foreign body-catching arms 5 are bundled together at the proximal ends and inserted into a connecting pipe 9 and secured therein. The connecting pipe 9 is secured to the distal end of the control wire 8 in the sheath 1. Thus, the foreign body-catching arms S are connected to the control wire 8 through the connecting pipe 9.

Accordingly, when the control wire 8 is pushed in the sheath 1 from the proximal end thereof, the foreign body-catching arms 5 expand in a petal-like shape by their own elasticity, as shown in FIG. 5. When the control wire 8 is pulled toward the proximal end of the sheath 1, the foreign body-catching arms 5 are withdrawn into the distal end of the sheath 1 and elastically deformed to be folded, as shown in FIG. 6.

Each foreign body-catching arm 5, arranged as stated above, has an engaging portion 10 at the distal end thereof for engagement with a foreign body that is to be recovered from a body cavity. The engaging portion 10 is bent outward in the open-close direction of the foreign body-catching arm 5 to form a U-shaped hook. When the foreign body-catching arms 5 are withdrawn into the sheath 1, as shown in FIG. 6, the engaging portions 10 lie adjacent to the distal end surface of the sheath 1.

Figure 7:
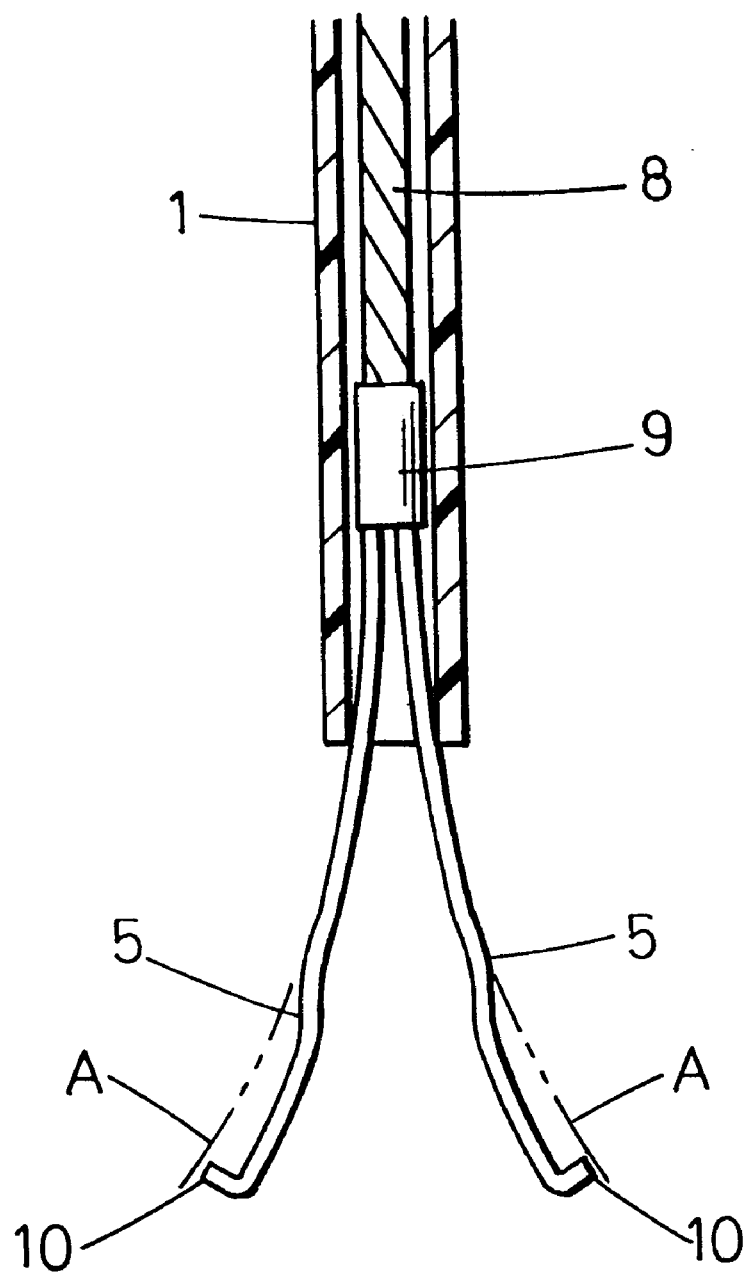
FIG. 7 is a sectional side view of a distal end portion of a foreign body-recovering instrument for an endoscope according to a fourth embodiment of the present invention, showing a state where foreign body-catching arms are open.
Figure 8:
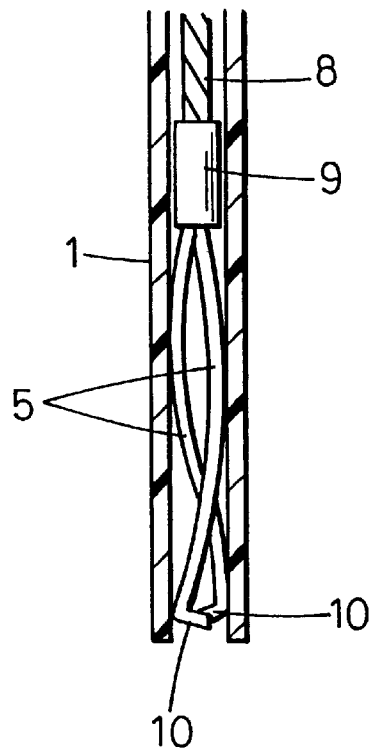
FIG. 8 is a sectional side view of the distal end portion of the foreign body-recovering instrument according to the fourth embodiment of the present invention, showing a state where the foreign body-catching arms are closed.

FIGS. 7 and 8 show a distal end portion of a foreign body-recovering instrument for an endoscope according to a fourth embodiment of the present invention. FIG. 7 shows a state where the distal end portion of the foreign body-recovering instrument is open. FIG. 8 shows a state where the distal end portion of the foreign body-recovering instrument is closed. In this embodiment, foreign body-catching arms 5 are each formed from a resilient wire. The distal end of each foreign body-catching arm 5 is bent outward at approximately right angles to form a hook-shaped engaging portion 10.

As shown in FIG. 7, the distal end half of the intermediate portion of each foreign body-catching arm 5 is bent to deflect slightly inward so that the distal end of the hook-shaped engaging portion 10 lies inside the extension A of the outer wall surface of the foreign body-catching arm 5.

Consequently, as shown in FIG. 8, the foreign body-catching arms 5 can be withdrawn into the sheath 1 completely so that the engaging portions 10 at the distal ends of the foreign body-catching arms 5 are also withdrawn into the sheath 1. The arrangement of the rest of this embodiment is the same as in the third embodiment.

Figure 9:
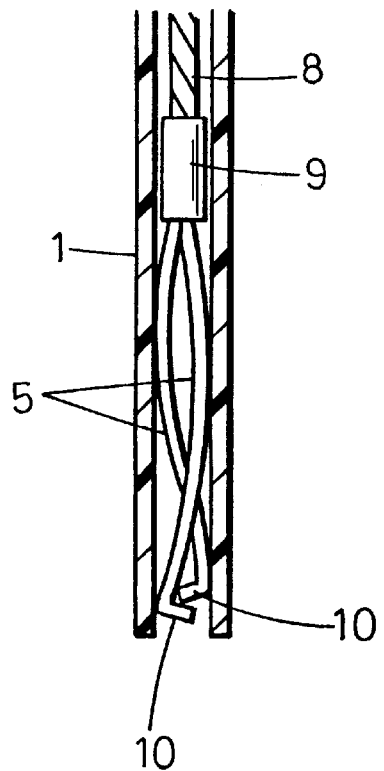
FIG. 9 is a sectional side view of a distal end portion of a foreign body-recovering instrument for an endoscope according to a fifth embodiment of the present invention, showing a state where foreign body-catching arms are closed.

FIG. 9 shows a distal end portion of a foreign body-recovering instrument for an endoscope according to a fifth embodiment of the present invention in a state where the distal end portion is closed. This embodiment is the same as the fourth embodiment except that a plurality of foreign body-catching arms 5 have slightly different lengths. Because of the different lengths of the foreign body-catching arms 5, the engaging portions 10 will not interfere with each other in the sheath 1. Therefore, the engaging portions 10 can be received into the sheath 1 even more easily.

Figure 10:
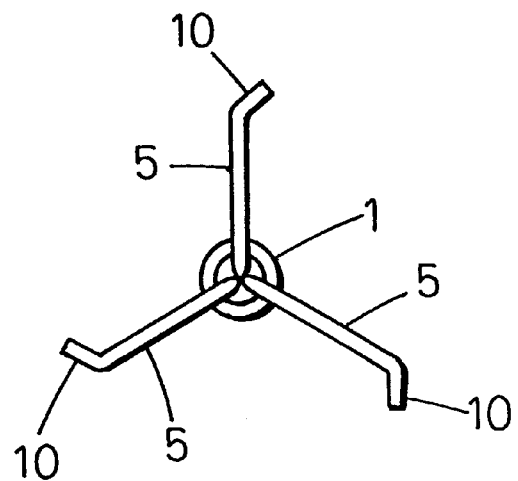
FIG. 10 is a front view of a distal end portion of a foreign body-recovering instrument for an endoscope according to a sixth embodiment of the present invention, showing a state where foreign body-catching arms are open.

FIG. 10 shows a distal end portion of a foreign body-recovering instrument for an endoscope according to a sixth embodiment of the present invention in a state where the distal end portion is open. This embodiment differs from the fourth embodiment, which is shown in FIGS. 7 and 8, only in the direction in which the engaging portions 10 project from the respective foreign body-catching arms 5.

In this embodiment, each engaging portion 10 is bent not directly outward in the open-close direction of the foreign body-catching arm 5 but obliquely outward, i.e. in a direction that is halfway between outward and sideward directions.

Figure 11:
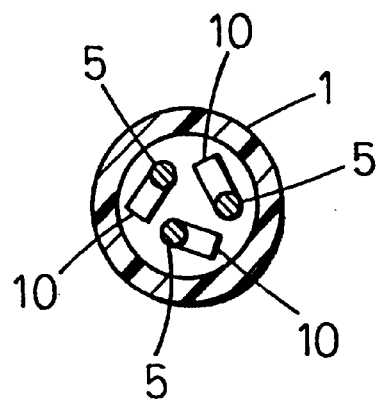
FIG. 11 is a sectional front view of the distal end portion of the foreign body-recovering instrument according to the sixth embodiment of the present invention, showing a state where the foreign body-catching arms are closed.
Figure 12:
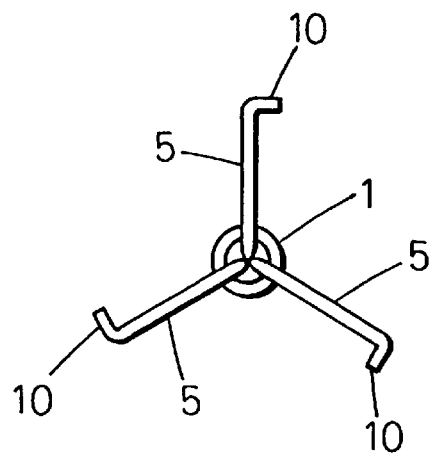
FIG. 12 is a front view of a distal end portion of a foreign body-recovering instrument for an endoscope according to a seventh embodiment of the present invention, showing a state where foreign body-catching arms are open.

By virtue of the above-described arrangement, when the foreign body-catching arms 5 are withdrawn into the sheath 1, the engaging portions 10 can be received in the sheath 1 without interfering with each other, as shown in FIG. 11. It should be noted that each engaging portion 10 may be bent sideward with respect to the open-close direction of the foreign body-catching arm 5 as in a seventh embodiment shown in FIG. 12.

Figure 13:
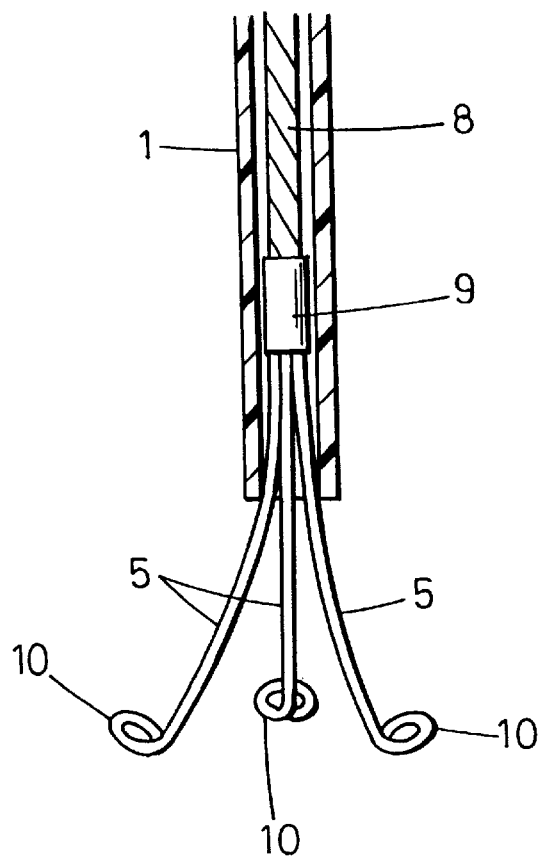
FIG. 13 is a sectional side view of a distal end portion of a foreign body-recovering instrument for an endoscope according to an eighth embodiment of the present invention, showing a state where foreign body-catching arms are open.

FIG. 13 shows a distal end portion of a foreign body-recovering instrument for an endoscope according to an eighth embodiment of the present invention in a state where the distal end portion is open. This embodiment differs from the third embodiment, which is shown in FIGS. 5 and 6, only in the shape of the engaging portions 10. In this embodiment, the distal end portion of each foreign body-catching arm 5 is bent outward in a small ring shape to form an engaging portion 10.

Figure 14:
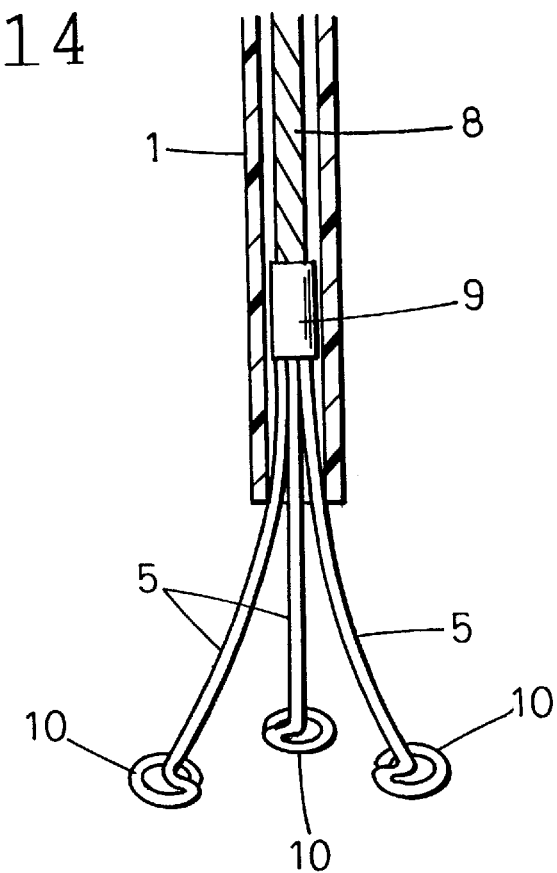
FIG. 14 is a sectional side view of a distal end portion of a foreign body-recovering instrument for an endoscope according to a ninth embodiment of the present invention, showing a state where foreign body-catching arms are open.

It should be noted that, as shown in a ninth embodiment shown in FIG. 14, the ring-shaped engaging portions 10 may be formed to project both inward and outward from the distal ends of the foreign body-catching arms 5. With this arrangement, the foreign body-recovering instrument can also be used in the same way as in the case of the conventional foreign body-recovering instrument, which recovers a foreign body by pinching it inside the foreign body-catching arms.

FIGS. 15 to 20 show examples of use of the foreign body-recovering instrument for an endoscope according to the present invention. The foreign body-recovering instrument shown in each of FIGS. 15 to 20 is one of the above-described embodiments. Any of the foreign body-recovering instruments according to the embodiments may be used for each method of use. In any case, the foreign body-recovering instrument is inserted into an instrument-inserting channel of an endoscope.

Figure 15:
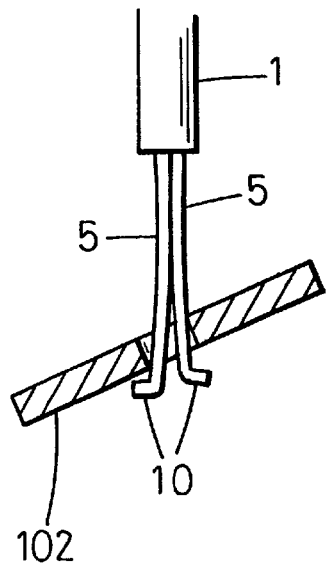
FIG. 15 is a schematic view showing an example of use of the foreign body-recovering instrument for an endoscope according to the present invention.

FIG. 15 shows the way in which the foreign body-recovering instrument is used to recover a coin 102 with a hole in the center. The foreign body-catching arms 5 are passed through the hole of the coin 102 and then actuated to open. Consequently, the hook-shaped engaging portions 10 are engaged with the back of the coin 102. Therefore, the coin 102 can be readily recovered without dropping.

Figure 16:
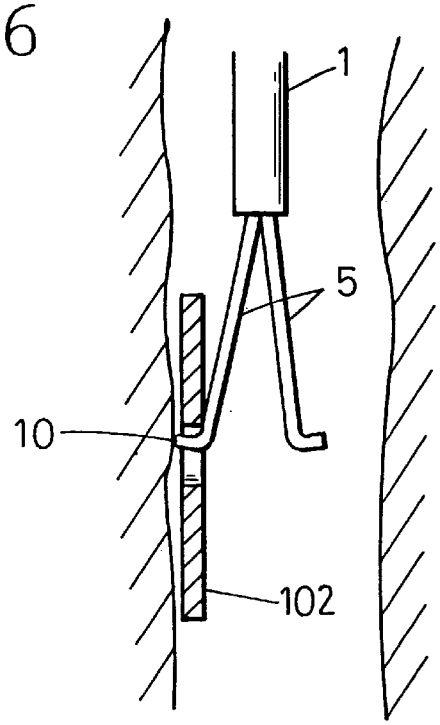
FIG. 16 is a schematic view showing an example of use of the foreign body-recovering instrument for an endoscope according to the present invention.

As shown in FIG. 16, to recover a coin 102 from a narrow tubular cavity in which the coin 102 cannot be carried in a transverse position, only one foreign body-catching arm 5 is passed through the hole of the coin 102, and the engaging portion 10 is engaged in the hole. In this state, the coin 102 is recovered.

Figure 17:
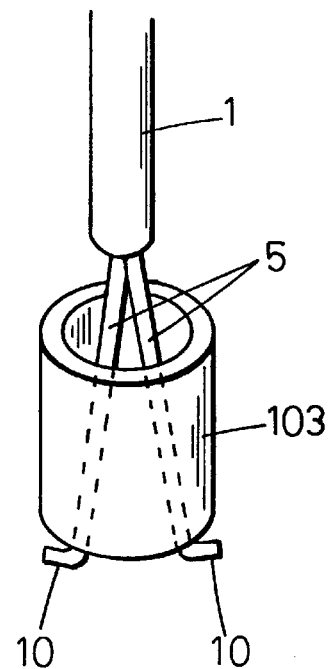
FIG. 17 is a schematic view showing an example of use of the foreign body-recovering instrument for an endoscope according to the present invention.

As shown in FIG. 17, to recover a tubular small article 103 swallowed into a body cavity, the foreign body-catching arms 5 are passed through the tubular small article 103 and then actuated to open. Consequently, the hook-shaped engaging portions 10 are engaged with the end surface on the reverse side of the small article 103. Therefore, the small article 103 can be recovered without dropping.

Figure 18:
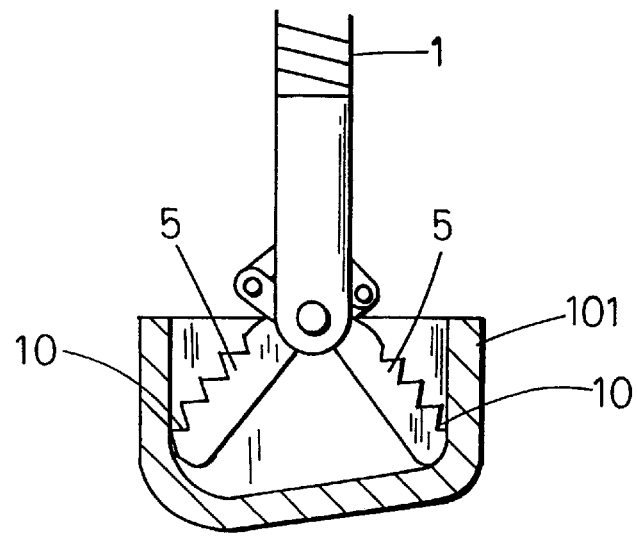
FIG. 18 is a schematic view showing an example of use of the foreign body-recovering instrument for an endoscope according to the present invention.

To recover a dental crown 101, as shown in FIG. 18, the foreign body-catching arms 5 are inserted into the dental crown 101 and then expanded. Consequently, the engaging portions 10, which are formed on the outer surfaces of the foreign body-catching arms 5, are engaged with the inner peripheral surface of the dental crown 101. Therefore, the dental crown 101 can be recovered without dropping. Although the foreign body-recovering instrument according to the second embodiment, shown in FIGS. 3 and 4, is shown in FIG. 18, it should be noted that the foreign body-recovering instruments according to the other embodiments can also catch and recover the dental crown 101 in the same way as the above.

Figure 19:
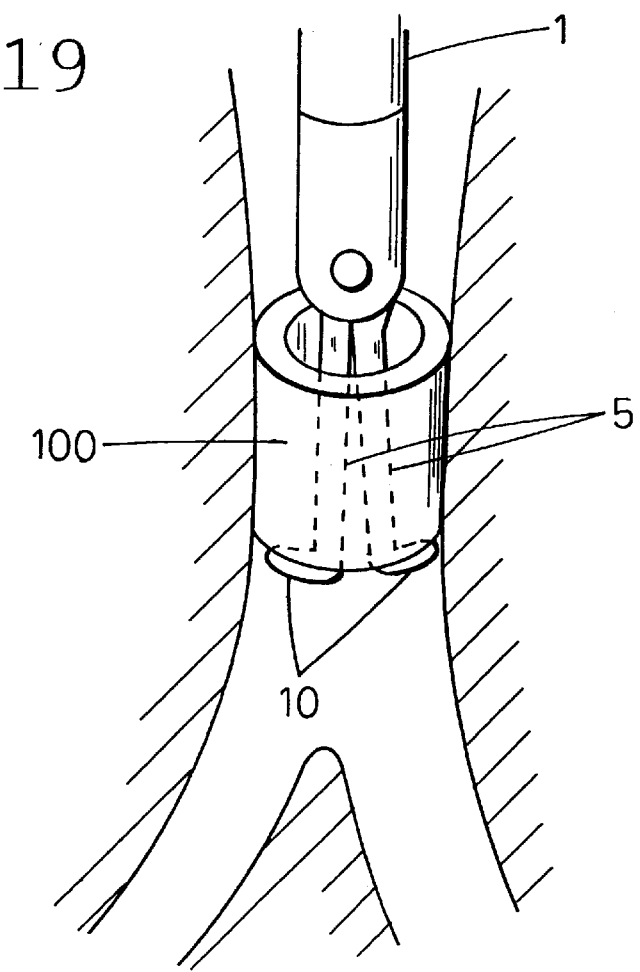
FIG. 19 is a schematic view showing an example of use of the foreign body-recovering instrument for an endoscope according to the present invention.

Thus, the foreign body-recovering instrument according to the present invention enables the foreign body-catching arms 5 to be engaged with a foreign body from inside it. Therefore, even when a foreign body 100 is lodged in a narrow tubular cavity such as a bronchial tube as shown in FIG. 19, the foreign body-catching arms 5 can be engaged with the foreign body 100. Thus, the foreign body 100 can be readily recovered from the narrow tubular cavity.

Figure 20:
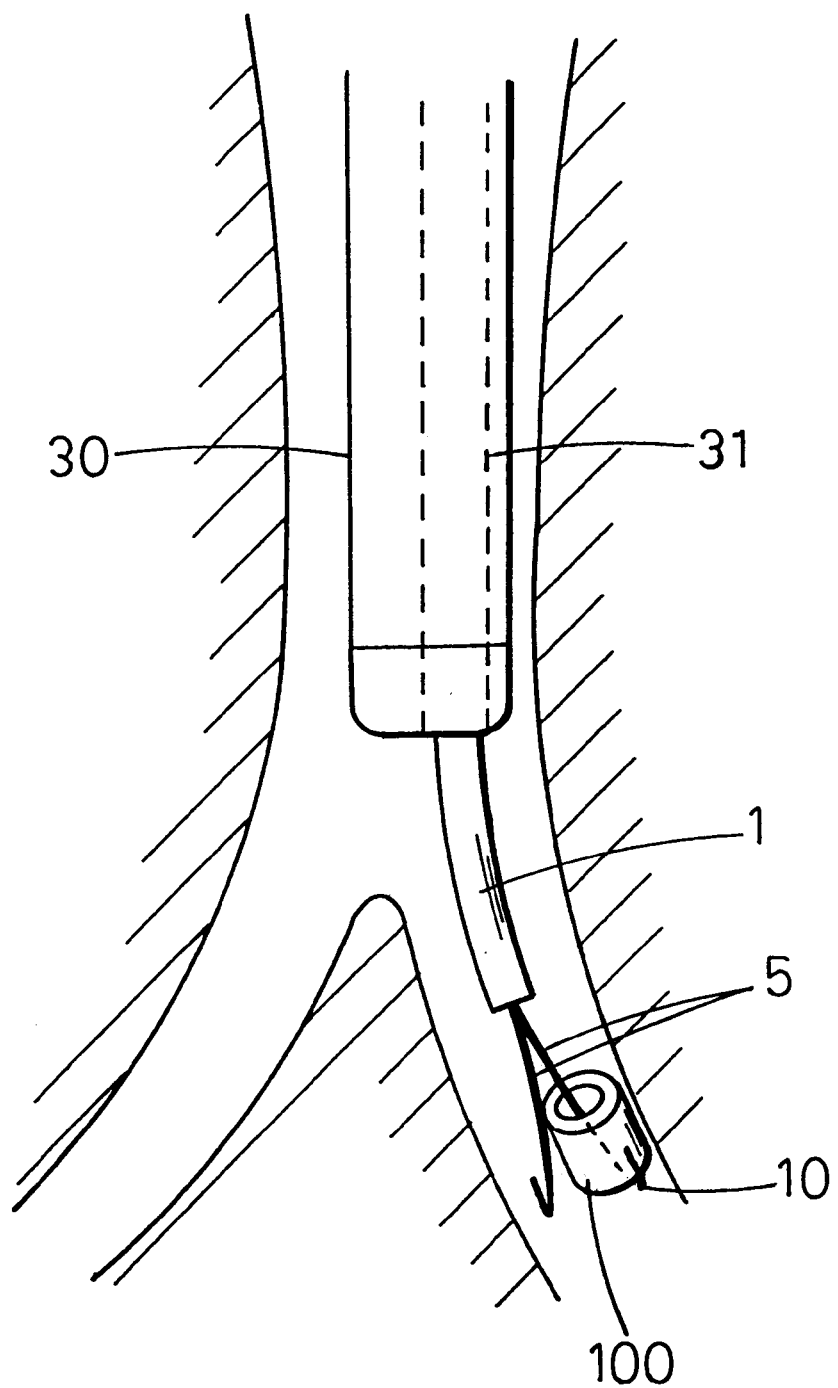
FIG. 20 is a schematic view showing an example of use of the foreign body-recovering instrument for an endoscope according to the present invention.
Figure 21:
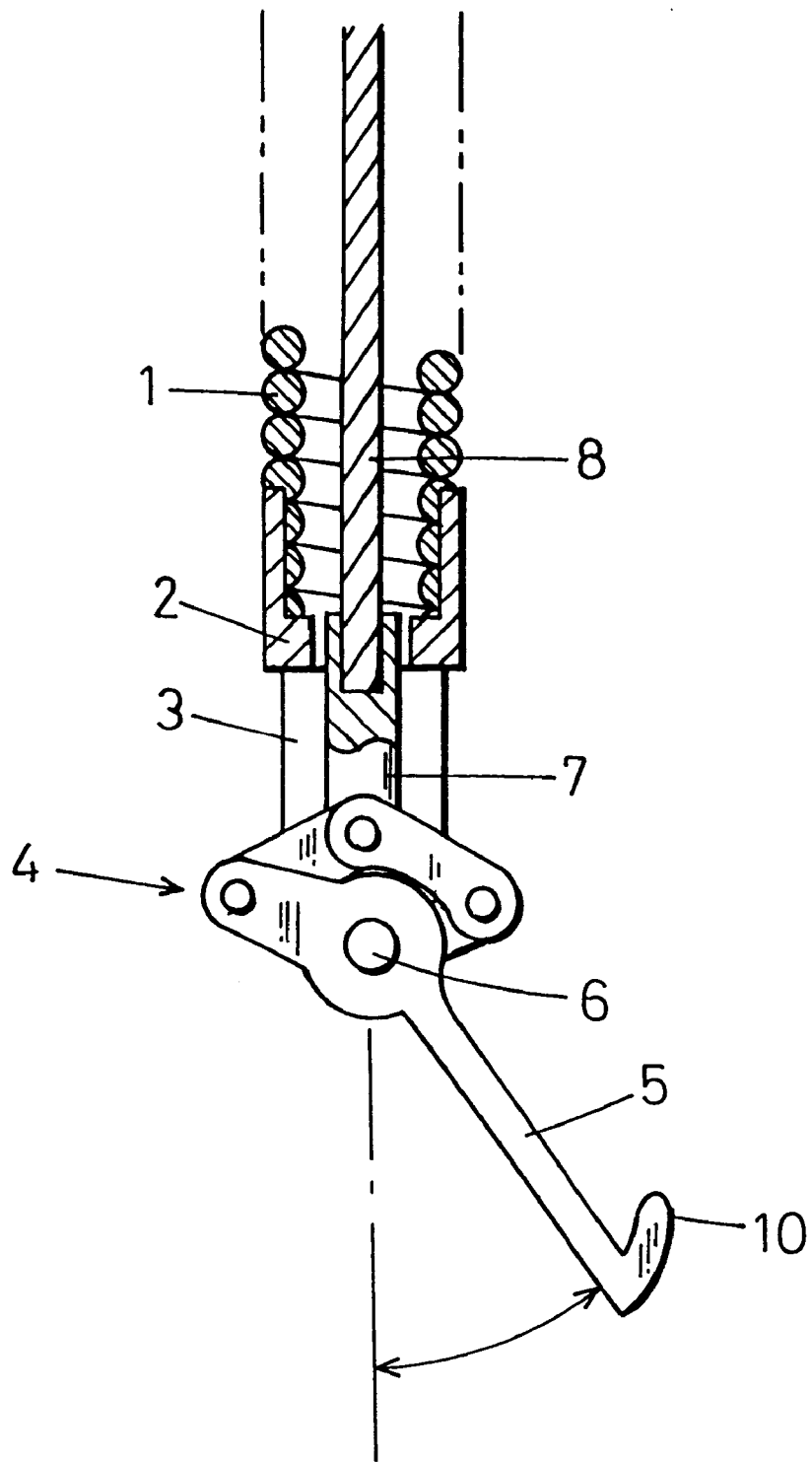
FIG. 21 is a sectional side view of a foreign body-recovering instrument for an endoscope that has a single foreign body-catching arm.
Figure 22:
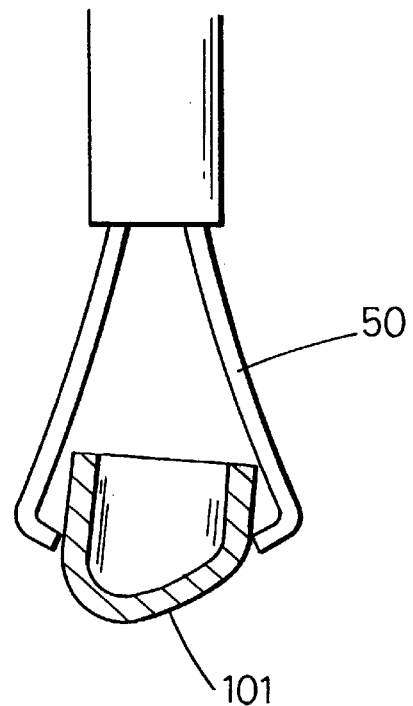
FIG. 22 is a schematic view showing an example of use of a conventional foreign body-recovering instrument for an endoscope.
Figure 23:
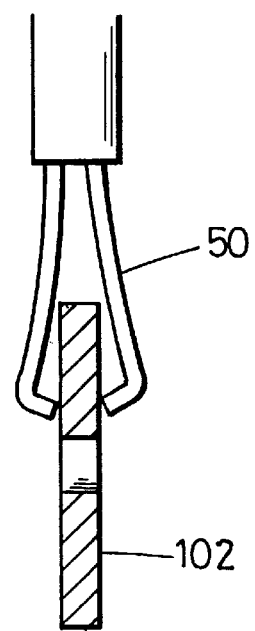
FIG. 23 is a schematic view showing an example of use of the conventional foreign body-recovering instrument.
Figure 24:
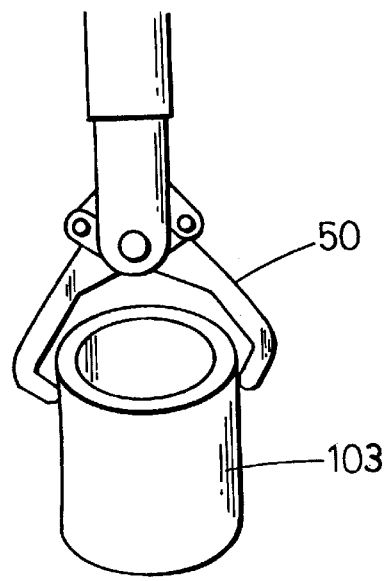
FIG. 24 is a schematic view showing an example of use of the conventional foreign body-recovering instrument.
Figure 25:
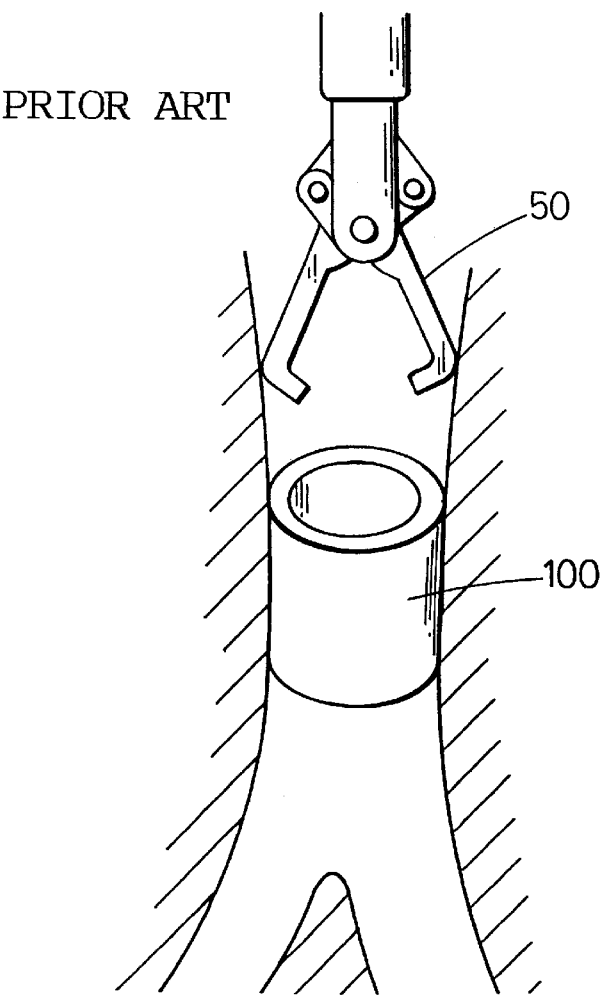
FIG. 25 is a schematic view showing an example of use of the conventional foreign body-recovering instrument.

As shown in FIG. 20, a small foreign body 100 can be recovered by engaging only one of a plurality of foreign body-catching arms 5 with the foreign body 100. In the figure, reference numeral 30 denotes an endoscope, and reference numeral 31 denotes an instrument-inserting channel. When used in this way, the foreign body-recovering instrument may be arranged to have only one foreign body-catching arm 5 as shown in FIG. 21.

According to the present invention, the outer surfaces of a plurality of foreign body-catching arms are provided with engaging portions serving as hooks for catching a foreign body. Therefore, the foreign body-catching arms can be engaged with a foreign body from inside it. Accordingly, a foreign body that has heretofore been difficult to catch and recover by pinching can be readily caught and recovered, depending upon the shape of the foreign body.

While the invention has been described by reference to specific embodiments chosen for purposes of illustration, it should be apparent that numerous modifications could be made thereto by those skilled in the art without departing from the basic concept and scope of the invention.

What is claimed is:

1. A foreign body-recovering instrument for an endoscope in which a plurality of foreign body-catching arms are provided at a distal end of a flexible sheath so that the foreign body-catching arms are opened or closed by remote control from a proximal end of the sheath, each of the foreign body-catching arms including inner sides and outer sides, said foreign body-recovering instrument comprising:

engaging portions comprising hooking members that engage and catch a foreign body, said engaging portions being formed on respective outer sides of said foreign body catching arms.

2. A foreign body-recovering instrument according to claim 1, wherein said engaging portions project outward or sideward from distal ends of said foreign body-catching arms in a hook-like shape.

3. A foreign body-recovering instrument according to claim 2, wherein said engaging portions project outward or sideward from the distal ends of said foreign body-catching arms in an L- or U-shape.

4. A foreign body-recovering instrument according to claim 3, wherein each of said foreign body-catching arms is bent at an intermediate portion thereof so that a distal end portion of said foreign body-catching arm is deflected inward with respect to a proximal end portion of said foreign body-catching arm.

5. A foreign body-recovering instrument according to claim 3, wherein each of said engaging portions has a ring shape.

6. A foreign body-recovering instrument according to claim 5, wherein said engaging portions project both outward and sideward from the distal ends of said foreign body-catching arms.

7. A foreign body-recovering instrument according to claim 1, wherein said engaging portions are provided with uneven surfaces on outer surface portions of said foreign body-catching arms.

8. A foreign body-recovering instrument according to claim 7, wherein said uneven surfaces comprise serrations.

9. The foreign body-recovering instrument according to claim 1, said foreign body-catching arms being movable into and out of the sheath, each of said plurality of foreign body-catching arms comprising a resilient member having a curved shape so as to expand outwardly as each said foreign body-catching arm moves out of the sheath.

10. The foreign body-recovering instrument according to claim 1, said foreign body-catching arms being movable into and out of the sheath, free ends of each of said foreign body catching arms being positioned adjacent to the distal end of the sheath when said foreign body-catching arms are moved into the sheath.

11. The foreign body-recovering instrument according to claim 1, an intermediate portion of each of said plurality of foreign body-catching arms being bent to extend inwardly so that the distal end of the engaging portion lies inside an extension of the outer surface of the foreign body-catching arm.

12. The foreign body-recovering instrument according to claim 1, each of said plurality of foreign body-catching arms having a different length.

13. The foreign body-recovering instrument according to claim 1, said foreign body-catching arms being movable into and out of the sheath, each engaging portion of said foreign body-catching arms extending at an oblique angle to a direction of movement of the foreign body-catching arm into and out of the sheath.

14. The foreign body-recovering instrument according to claim 1, a shape of each of said engaging portions comprising an annular ring.

15. The foreign body-recovering instrument according to claim 1, said plurality of foreign body-catching arms comprising at least three arms.

16. The foreign body-recovering instrument according to claim 1, said foreign body-catching arms being pivotally mounted for opening and closing movement.

* * * * *

UNITED STATES PATENT AND TRADEMARK OFFICE
CERTIFICATE OF CORRECTION

PATENT NO.     : 6,206,904 B1                                    Page 1 of 1
DATED          : March 27, 2001
INVENTOR(S)    : Teruo Ouchi It is certified that error appears in the above-identified patent and that said Letters Patent is hereby corrected as shown below:

<u>Title page,</u>
Item [73], Assignee: "Ashai Kogaku Kogyo Kabushiki Kaisha, Tokyo (JP)"
should be -- Asahi Kogaku Kogyo Kabushiki Kaisha, Tokyo (JP) --

Signed and Sealed this

Second Day of April, 2002

Attest:

*Attesting Officer*

JAMES E. ROGAN
*Director of the United States Patent and Trademark Office*